(12) United States Patent
Trapp

(10) Patent No.: US 8,297,135 B2
(45) Date of Patent: Oct. 30, 2012

(54) ANALYSIS OF SUBSTANCE MIXTURES

(75) Inventor: Oliver Trapp, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 498 days.

(21) Appl. No.: 12/090,687

(22) PCT Filed: Oct. 17, 2006

(86) PCT No.: PCT/DE2006/001834
§ 371 (c)(1),
(2), (4) Date: Apr. 18, 2008

(87) PCT Pub. No.: WO2007/045224
PCT Pub. Date: Apr. 26, 2007

(65) Prior Publication Data
US 2008/0295617 A1    Dec. 4, 2008

(30) Foreign Application Priority Data
Oct. 18, 2005   (DE) .......................... 10 2005 050 114

(51) Int. Cl.
G01N 33/00  (2006.01)
G01N 30/16  (2006.01)
G01N 30/86  (2006.01)
B01D 50/00  (2006.01)

(52) U.S. Cl. ...... 73/866; 73/23.41; 73/863.21; 204/450; 702/31; 702/32

(58) Field of Classification Search .................. 73/23.36, 73/23.41, 61.55, 61.57, 64.56, 863, 863.21, 73/866; 204/450, 457, 461; 702/22, 24, 702/31–32
See application file for complete search history.

(56) References Cited

U.S. PATENT DOCUMENTS

| | | | | |
|---|---|---|---|---|
| 4,006,350 A * | 2/1977 | Jokl | ................................ | 702/25 |
| 5,744,654 A * | 4/1998 | Waters | .......................... | 568/750 |
| 5,954,862 A * | 9/1999 | Wilson | ............................ | 96/101 |
| 6,054,683 A * | 4/2000 | Bremer et al. | ................ | 219/388 |
| 6,495,016 B1 * | 12/2002 | Nawracala | ..................... | 204/604 |
| 6,589,760 B1 * | 7/2003 | Buchanan et al. | .............. | 435/23 |
| 6,929,780 B2 * | 8/2005 | Gerstel | ........................... | 422/89 |
| 2004/0144918 A1 | 7/2004 | Zare et al. | | |

FOREIGN PATENT DOCUMENTS

| | | |
|---|---|---|
| DE | 25 14 340 | 10/1975 |
| DE | 199 49 551 | 5/2001 |
| EP | 685738 A1 * | 12/1995 |

(Continued)

*Primary Examiner* — Thomas P Noland
(74) *Attorney, Agent, or Firm* — Norris McLaughlin & Marcus, P.A.

(57) ABSTRACT

The invention relates to a method for substance mixtures, particularly complex chemical and/or biochemical substance mixtures. According to said method, a substance mixture that is to be analyzed is fed to a separating device, the substances of the substance mixture that is to be analyzed are separated from each other in the separating device by means of a chemically and/or physically induced conveying process, and the separated substances are detected in an evaluation unit. The invention further relates to methods and devices for producing pulsed substance mixtures, particularly complex chemical and/or biochemical substance mixtures. In order to improve the analysis of substance mixtures especially regarding the duration of the analysis, the throughput, and the resolution, the substance mixture that is to be analyzed is fed to the separating device in pulses having an unique binary sequence.

13 Claims, 7 Drawing Sheets

FOREIGN PATENT DOCUMENTS

| | | | |
|---|---|---|---|
| GB | 1 150 266 | 4/1969 | |
| GB | 2039777 A * | 8/1980 | ................. 73/864.81 |
| GB | 2 268 096 | 1/1994 | |
| WO | WO 0151179 A1 * | 7/2001 | |
| WO | WO 0239106 A1 * | 5/2002 | |
| WO | WO 03067250 A1 * | 8/2003 | |

* cited by examiner

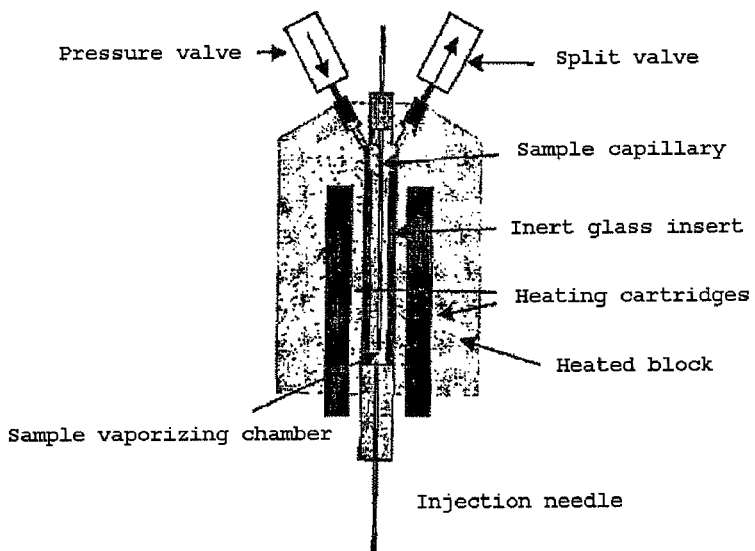
Fig. 3
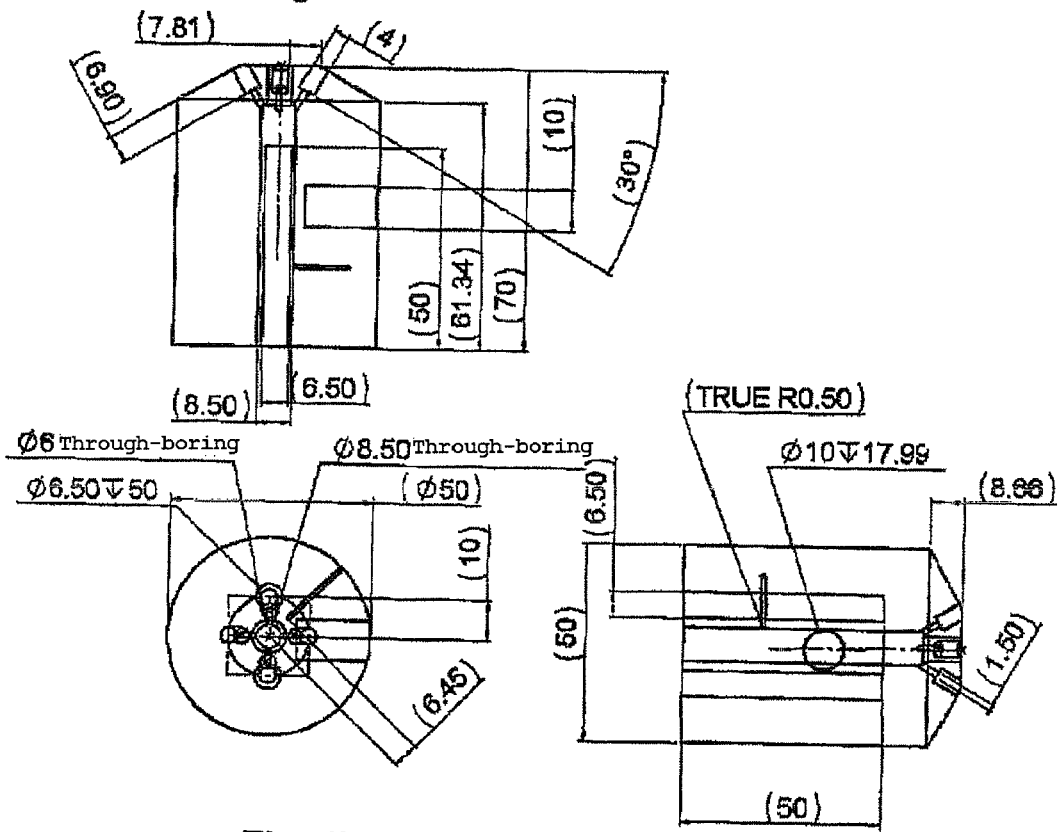
Fig. 4a
Fig. 4b  Fig. 4c

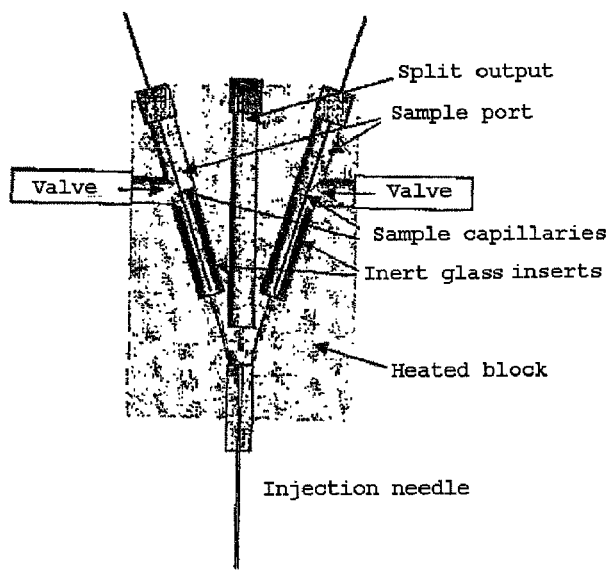
Fig. 5
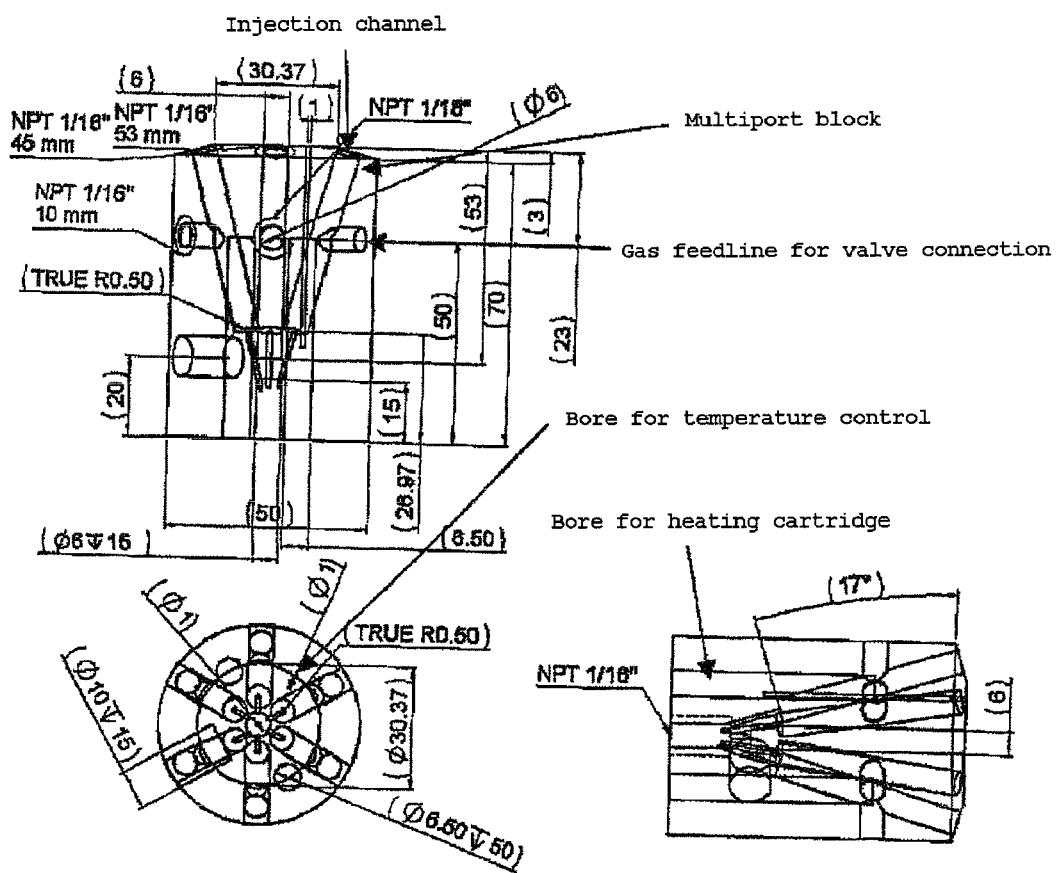
Fig. 6a
Fig. 6b
Fig. 6c

ANALYSIS OF SUBSTANCE MIXTURES

This application is a 371 of PCT/DE2006/001834, filed Oct. 17, 2006, which claims foreign priority benefit under 35 U.S.C. §119 of the German Patent Application No. 10 2005 050 114.1 filed Oct. 18, 2005.

The present invention relates to a method for analyzing substance mixtures, in particular complex chemical and/or biochemical substance mixtures, a substance mixture to be analyzed being fed to a separating device, the substances of the substance mixture to be analyzed being separated from one another by the separating device by chemically and/or physically effected transport, and the substances separated from one another being detected by an evaluation device.

The present invention further relates to methods and apparatuses for producing pulsed substance mixtures, in particular complex chemical and/or biochemical substance mixtures, preferably for use with an inventive analysis of substance mixtures, in particular complex chemical and/or biochemical substance mixtures.

Various methods and apparatuses are known in the prior art for qualitative and/or quantitative analysis, that is to say for determining the type and/or quantity of the components of a substance mixture, which use chemical/physical and/or biochemical methods and various separating techniques.

In order to identify and/or quantify chemical compounds in complex chemical and/or biochemical substance mixtures to be analyzed, particularly in the case of the analysis of complex chemical substance mixtures from high throughput methods, in particular from parallelized chemical reactors, or in the case of the examination of combinatorial substance libraries, and/or the analysis of natural substances, proteins, peptides and/or such biochemically relevant compounds, for example to be analyzed in a so-called genome, proteome, metabolome, and/or transcriptome analysis, use is made, in particular, of chromatographic or electrophoretic separating methods and/or devices, where the substance mixtures to be analyzed are analyzed sequentially and/or in parallel.

Furthermore, for the purpose of analysis, the separating devices are generally coupled or connected to an evaluation device for sensing or detecting the mutually separated substances of the substance mixture. The evaluation devices or detectors may use, in this case, in particular spectroscopic and/or spectrometric detection techniques in conjunction with genome, proteome, metabolome and/or transcriptome analyses, use may be made, in particular, of spectroscopic detectors, for example in nuclear magnetic resonance (NMR) spectroscopy or infrared (IR) spectroscopy, and of mass spectrometric (MS) detectors.

The previously known methods and devices for analyzing substance mixtures, in particular complex chemical and/or biochemical substance mixtures, have various disadvantages. Thus, owing to long analysis periods and to low detection sensitivities or poor signal-to-noise ratios (SNRs) of the evaluation devices brought into use, the previously known methods and devices using high-resolution spectroscopic and/or spectrometric techniques, in particular, are limited. As a rule, it is impossible here to analyze very small amounts of substances when detecting the entire spectroscopic or spectrometric range of a substance mixture to be analyzed. However, the throughput of substance mixtures to be analyzed is severely limited, particularly because of the long analysis periods required to date. Thus, for example, the quantitative and qualitative analysis of the educts and products of a 7-times-7 parallel reactor requires approximately 24.5 h in conjunction with an analysis period of approximately 30 min in each case.

In view of this prior art, it is the object of the present invention to improve the analysis of substance mixtures when avoiding the disadvantages described, particularly with regard to the analysis period, throughput and resolution.

To achieve the technical solution, the present invention proposes a method for analyzing substance mixtures, in particular complex chemical and/or biochemical substance mixtures, a substance mixture to be analyzed being fed to a separating device, the substances of the substance mixture to be analyzed being separated from one another by the separating device by chemically and/or physically effected transport, and the substances separated from one another being detected by an evaluation device, in the case of which method the substance mixture to be analyzed is fed to the separating device in pulses of a unique binary sequence.

The invention is based on the finding that using a substance mixture to be analyzed with pulses of a unique binary sequence, that is to say a sequence comprising an arbitrary succession of zeroes ("0") and ones ("1"), yields a substance mixture to be analyzed that is provided with an identifier, particularly in the manner of a barcode, with the result that it is simultaneously possible for different substance mixtures to be fed to the analysis—something in the manner of a multiplexing method similar to US 2004/0144918 A1 for applications in spectroscopy (FT-NMR, FT-IR) and mass spectrometry (FT-ICR-MS and HT-TOF-MS)— so that it is possible, in particular, to improve the analysis period, the throughput of substance mixture to be analyzed and the resolution of the analyzed substances. According to the invention, a number of substance mixture analyses can thus advantageously be carried out with the result that, in particular, the signal-to-noise ratio (SNR) is further improved.

It is preferred that the pulses of the substance mixture to be analyzed are fed to the separating device in a fashion temporally and spatially separated from one another.

In an advantageous refinement of the invention, the unique binary sequence is produced with a binary random number generator. In a further advantageous refinement of the invention, the unique binary sequence is formed from a sequence that is subdivided by a repeating sequence and generated with a binary random number generator. Owing to these inventive measures, a so-called pseudorandom sequence is generated, and it is advantageously ensured that the sequence of the pulses of the substance mixture to be analyzed does not repeat. The overall result is thus to improve the uniqueness of the binary pulse sequence.

In accordance with a further advantageous proposal of the invention, the unique binary sequence consists of $2^n$ elements, with $0 \leq n \leq \infty$ (at least theoretically), preferably with $5 \leq n \leq 128$, and particularly preferably with $7 \leq n \leq 14$. The invention makes use of the finding that n analyses can be carried out in the same time as a conventional analysis. Consequently, the signal-to-noise ratio (SNR) can be improved in a range from $$\sqrt{\frac{n}{2}} \geq SNR \geq \frac{\sqrt{n}}{2}.$$

The maximum achievable improvement in the signal-to-noise ratio (SNRs) is consequently $$\frac{\sqrt{n}}{2}.$$

The longer the pulse sequences that are used, the greater becomes the advantage in the signal-to-noise ratio (SNR), the so-called Felgett advantage, and there is consequently an improvement in the resolution and the clarity of the assignment of the signals of the substances detected by the evaluation unit.

A further refinement of the invention is characterized by a modulation interval with a sequence or pulse interval duration ($\Delta t$) in a range from approximately 0.25 s to approximately 20 s, preferably in a range from approximately 1 s to approximately 20 s. A further advantageous refinement of the invention provides a pulse duration ($\Delta t_{pulse}$) in a range from approximately 1 ms to approximately 1 s, preferably in a range from approximately 1 ms to approximately 10 ms. According to the invention, it is thus possible to generate high-precision pulsed sequences of the substance mixture to be analyzed that lead, in particular, to a further improvement in the throughput and the resolution.

Substance detection by the evaluation device is advantageously performed in a fashion synchronized with the substance mixture feed. In one preferred refinement of the invention, the evaluation device is operated with a detection period that corresponds to the pulse interval duration ($\Delta t$) or to an integral fraction of the pulse interval duration ($\Delta t$). It is thereby advantageously possible to implement a so-called oversampling of the pulse sequence. According to the invention, the evaluation device can thus make use, for the purpose of detecting the substances of the substance mixture to be analyzed, of detectors that are driven by comparison with the pulse interval duration ($\Delta t$) with shorter detection times, that is to say are driven more slowly, in particular. According to the invention, it is thus advantageously possible to detect substances of the substance mixture to be analyzed in the entire detection range of the detector of the evaluation device.

A particularly advantageous refinement of the invention provides that the substances detected by the evaluation device are deconvoluted mathematically with the unique binary sequence of the pulses of the substance mixture to be analyzed, preferably by a two-dimensional mathematical deconvolution. Advantageously, in the course of the deconvolution, the substances detected by the evaluation device are subjected to a Hadamard transformation with the unique binary sequence, the concentration distributions of the substances detected by the evaluation device are determined from the result of the Hadamard transformation, and the concentrations of the individual substances detected by the evaluation device are determined, preferably by using the concentrations of the individual substances detected by the evaluation device to solve a system of linear equations formed by the concentration distributions, the concentrations of the individual substances detected by the evaluation device, and the substances detected by the evaluation device. Thus, owing to a two-dimensional mathematical deconvolution with the known pulse sequence of the substance mixture to be analyzed it is advantageously possible to determine the respective spectra of the substances of the substance mixture as a function of their respective retention time for the purpose of an identification and quantification, an improved signal-to-noise ratio (SNR) and an improved detection limit advantageously being achieved in comparison with previously known, in particular continuously operated analysis methods.

The inventive Hadamard transformation (HT) advantageously enables multiplexing of the substance mixture to be analyzed, by means of which up to three discrete states ("−1", "0", "+1") can advantageously be coded. The substance mixture to be analyzed is coded in this case as a wave or particle packet with the binary pseudorandom sequences (modulation sequence). Instead of the Hadamard matrix, it is advantageously possible to use a Simplex matrix derived therefrom that codes two discrete states ("0", "1") and can be obtained by Simple transformation from the Hadamard matrix as follows:

Delete the 1st column and 1st row $$H := \begin{bmatrix} + & + & + & + & + & + & + \\ -1 & -1 & -1 & 1 & -1 & 1 & 1 \\ -1 & -1 & 1 & -1 & 1 & 1 & -1 \\ -1 & 1 & -1 & 1 & 1 & -1 & -1 \\ 1 & -1 & 1 & 1 & -1 & -1 & -1 \\ -1 & 1 & 1 & -1 & -1 & -1 & 1 \\ 1 & 1 & -1 & -1 & -1 & 1 & -1 \\ 1 & -1 & -1 & -1 & 1 & -1 & 1 \end{bmatrix}$$

Exchange
−1 to 1
1 to 0 modulation sequence $$S := \begin{bmatrix} 1 & 1 & 1 & 0 & 1 & 0 & 0 \\ 1 & 1 & 0 & 1 & 0 & 0 & 1 \\ 1 & 0 & 1 & 0 & 0 & 1 & 1 \\ 0 & 1 & 0 & 0 & 1 & 1 & 1 \\ 1 & 0 & 0 & 1 & 1 & 1 & 0 \\ 0 & 0 & 1 & 1 & 1 & 0 & 1 \\ 0 & 1 & 1 & 1 & 0 & 1 & 0 \end{bmatrix}$$

simplex matrix

The mathematical deconvolution is preferably performed by multiplying the signal obtained by the inverse Hadamard matrix or Simplex matrix:

$$I_{rawdata} \times S^{-1} = I_{data}$$

The separating device advantageously uses chromatographic and/or electrophoretic separating methods and is preferably a gas chromatograph or a supercritical fluid chromatograph.

In a further advantageous refinement of the invention, the evaluation device comprises at least one detector and/or at least one spectroscopic and/or spectrometric detector.

In order to generate pulsed substance mixtures, in particular complex chemical and/or biochemical substance mixtures, it is proposed according to the method that at least one substance mixture is fed continuously to at least one channel via at least one capillary line, the substance mixture is vaporized in at least one deactivated glass tube arranged in the at least one channel, a gas flow is applied to the at least one channel via a switchable pressure valve, and vaporized substance mixture to which the gas flow has been applied is injected from the at least one channel into a needle.

The switchable pressure valve is advantageously switched with pulses of a unique binary sequence. According to the invention, switching times of the switchable pressure valve in a range from approximately 1 ms to approximately 1 s, preferably in a range from approximately 1 ms to approximately 10 ms are provided.

A further refinement of the invention provides applying to the vaporized substance mixture a gas flow that consists of a gas and/or a gas mixture and excludes variations in the composition of the vaporized substance mixture, with particular preference with an inert gas and/or inert gas mixture.

The gas flow is advantageously applied, preferably in a fashion controlled by the switchable pressure valve of the channel, in order to flush the at least one channel and/or the needle.

One refinement of the invention having at least two channels injecting into the needle provides that the respective switchable pressure valves of the channels are controlled synchronously with and/or separately from one another.

The vaporization of the substance mixture is advantageously controlled, preferably by controlling the temperature of a heating device for vaporizing the substance mixture. The pressure of the gas flow is advantageously controlled. A further improvement in the precision of the pulse sequences and their defined switching times can be achieved, in particular, by means of these measures, individually and/or in combination with one another.

There is proposed for the purpose of generating pulsed substance mixtures, in particular complex chemical and/or biochemical substance mixtures an apparatus that is characterized by at least one channel with at least one capillary line for feeding at least one substance mixture into the channel, with at least one deactivated glass tube, arranged in the channel, for vaporizing the at least one substance mixture fed to the channel, this being done in the channel with the aid of a heating device, and with a switchable pressure valve for connecting the channel to a gas feed line for applying a gas flow to the at least one vaporized substance mixture, and with an output, connected for flow purposes to the at least one channel, for connecting a gas discharge line, preferably an injection needle.

In a further refinement of the invention, the inflow direction of the gas flow for applying the at least one vaporized substance mixture via the switchable pressure valve assumes an angle in a range of approximately 0° to approximately 180° to the direction of longitudinal extent of the channel. The inflow direction of the gas flow for applying the at least one vaporized substance mixture advantageously runs substantially perpendicular to the direction of longitudinal extent of the channel. A further refinement of the invention provides that the gas feed line can be connected to the channel via the switchable pressure valve approximately in the middle of the direction of longitudinal extent of the channel. It can be ensured by means of the inventive refinements, individually and/or in combination with one another, that disturbances of the pulse sequence to be produced are not generated or generated by the application. Precision of the pulse sequence to be generated and of the individual pulses, in particular, can be improved thereby.

A further refinement of the invention provides that the heating device is arranged at least in the region of the deactivated glass tube arranged in the channel, the heating device preferably being designed in the form of an exchangeably arrangeable heating cartridge. The inventive refinement thus permits, in particular, a Simple and rapid exchange of the heating device. A further advantageous refinement of the invention provides the use of at least one sensor system element for detecting the temperature of the heating device and/or of the vaporization, the detected temperature preferably being capable of use for controlling the heating device. It is thereby possible, in particular, for the precision of the pulse sequence to be generated and of the individual pulses to be further controlled and improved.

The pressure valve of the inventive apparatus can advantageously be switched with switching times in a range from approximately 1 ms to approximately 1 s, preferably in a range from approximately 1 ms to approximately 10 ms.

The at least one capillary line of the inventive apparatus is advantageously made from metal, glass and/or fused silica glass. The inventive apparatus is advantageously fabricated from metal and/or a metal alloy, preferably in one piece.

The inventive method and the inventive apparatus are advantageously used to generate pulsed substance mixtures, in particular complex chemical and/or biochemical substance mixtures, with the aid of an inventive analysis method, the substance mixture to be analyzed being fed, or being capable of being fed, to the separating device via the needle.

In order to generate pulsed substance mixtures, in particular complex chemical and/or biochemical substance mixtures, it is further proposed according to the method that a continuous substance mixture flow is successively guided through at least two mutually separated chambers, the substance mixture flow being focused in the first chamber, and the focused substance mixture flow being modulated with pulses of a unique binary sequence in the second chamber.

The focusing of the substance mixture flow and/or the modulation of the focused substance mixture flow are/is advantageously performed by means of a cold and warm gas flow, the substance mixture flow firstly being frozen out and subsequently being released again by rapid heating.

In a further refinement of the invention, the chambers respectively have at least one cold gas jet nozzle and at least one warm gas jet nozzle whose nozzle openings respectively enable a cold or warm gas flow flowing substantially perpendicular to the flow direction of the substance mixture flow through the respective chamber. The nozzle openings of the at least one cold gas jet nozzle and the at least one warm gas jet nozzle of the respective chambers advantageously enable a substantially mutually perpendicular flow. The cold and/or warm gas jet nozzles of the respective chambers are advantageously operated with gas flows of up to 40 l/min.

A further refinement of the invention provides that at least the nozzles of the chamber enabling modulation of the focused substance mixture flow are driven with switching times in a range from approximately 1 ms to approximately 1 s, preferably in a range from approximately 1 ms to approximately 10 ms.

The nozzles of the at least two chambers are advantageously driven in a mutually separate and independent fashion. In a further refinement of the invention, the nozzles of the at least two chambers are driven in synchronous fashion, and are preferably driven with different sequences.

A further refinement of the invention provides a gas flow that consists of a gas and/or a gas mixture for the cold and/or warm gas flow and excludes variations in the composition of the vaporized substance mixture, with particular preference implemented by using an inert gas and/or inert gas mixture. The pressure of the respective gas flow is advantageously controlled.

In order to generate pulsed substance mixtures, in particular complex chemical and/or biochemical substance mixtures, there is further proposed an apparatus that is characterized by at least two mutually separated chambers, respectively having an inlet and an outlet, for guiding a continuous substance mixture flow through the respective chamber, the chambers being successively arranged in the flow direction of the substance mixture flow through the chambers, and the chambers respectively having at least one cold gas jet nozzle and at least one warm gas jet nozzle whose nozzle openings respectively enable a cold or warm gas flow flowing substantially perpendicular to the flow direction of the substance mixture flow through the respective chamber.

In a further refinement of the invention, the nozzle openings of the at least one cold gas jet nozzle and the at least one warm gas jet nozzle of the respective chambers are designed to enable a substantially mutually perpendicular flow.

The cold and/or warm gas jet nozzles of the respective chambers can advantageously be operated with gas flows of up to 40 l/min.

In a further advantageous refinement of the invention, the first chamber in the flow direction of the substance mixture flow is designed to enable focusing of the substance mixture flow, and the second chamber in the flow direction of the substance mixture flow is designed to enable modulation of the focused substance mixture flow with pulses of a unique binary sequence.

At least the nozzles of the chamber enabling modulation of the focused substance mixture flow can advantageously be driven with switching times in a range from approximately 1 ms to approximately 1 s, preferably in a range from approximately 1 ms to approximately 10 ms.

The further inventive method and the further inventive apparatus for generating pulsed substance mixtures, in particular complex chemical and/or biochemical substance mixtures, are advantageously used with an inventive analysis method, the substance mixture to be analyzed being fed, or being capable of being fed, to the separating device via the outlet of the second chamber.

BRIEF DESCRIPTION OF THE DRAWINGS

Further details, features and advantages of the invention are explained in more detail below with the aid of the exemplary embodiments of the invention that are illustrated in the figures of the drawing, in which:

FIG. 3 shows a schematic of the design of an exemplary embodiment of an inventive apparatus for generating pulsed substance mixtures;

FIGS. 4a to 4c show a schematic side, front and sectional view of the apparatus according to FIG. 3;

FIG. 5 shows a schematic of the design of a further exemplary embodiment of an inventive apparatus for generating pulsed substance mixtures;

FIGS. 6a to 6c show a schematic side, front and sectional view of the apparatus according to FIG. 5;

FIG. 1 and FIG. 2 respectively show a schematic of the principle of an exemplary embodiment of the design principle of an arrangement for carrying out an inventive analysis of substance mixtures, in particular complex chemical and/or biochemical substance mixtures. In this case, a substance mixture to be analyzed, which comes from a chemical reactor, is fed as a continuous flow to a device (injector) for generating pulsed substance mixtures. Exemplary embodiments of appropriate apparatuses for generating pulsed substance mixtures are illustrated in FIG. 3 to FIG. 7, and explained in more detail below in conjunction therewith. The continuous substance mixture flow of the substance mixture to be analyzed is supplied in the exemplary embodiment in accordance with FIG. 1 by a chemical reactor. The substance mixture pulses generated by the apparatus for generating pulsed substance mixtures are then passed to the separating column (fused silica column (fs column)) of a gas chromatograph (GC) serving as separating device. The substances of the substance mixture to be analyzed are separated from one another by the gas chromatograph (GC). The mutually separated substances are then detected by an evaluation device. The evaluation device is formed by a detector of the gas chromatograph in the exemplary embodiment illustrated in FIG. 1. In the case of the exemplary embodiment illustrated in FIG. 2, the evaluation device is a spectrometer coupled to the gas chromatograph (GC). The components of the arrangement, that is to say a control device (GC controller) of the gas chromatograph (GC), a data acquisition device and a device (modulation sequence), which is used as modulator by the device (injector) for generating substance mixture pulses and is connected to an amplifier, for generating a unique binary sequence of substance mixture pulses, are controlled in the present case by a computing device (computer) connected to the components.

Carrying out an inventive analysis of substance mixtures by means of multiplexing requires precise control of the injection of the substance mixture (analytes) into the chromatographic separating system. This control comprises, in particular, a precise and defined temporal control of the time interval between successive injections of the pulsed substance mixture into the separating device (gas chromatograph), as well as of the injection period within such a time interval. A precise and defined control of the quantity of the substance mixture (sample quantity) is also required.

The valve circuits so far coming into use in the prior art in order to generate pulsed substance mixtures, for example in the field of gas and fluid chromatography or of capillary electrophoresis are slow, and the control of the sample volume is inflexible, particularly owing to sample loops. Furthermore, a valve circuit coupled directly to the chromatographic system gives rise to pressure surges that lead to so-called system peaks in the chromatogram, since no continuous flow occurs in the chromatographic system.

Figure 1:
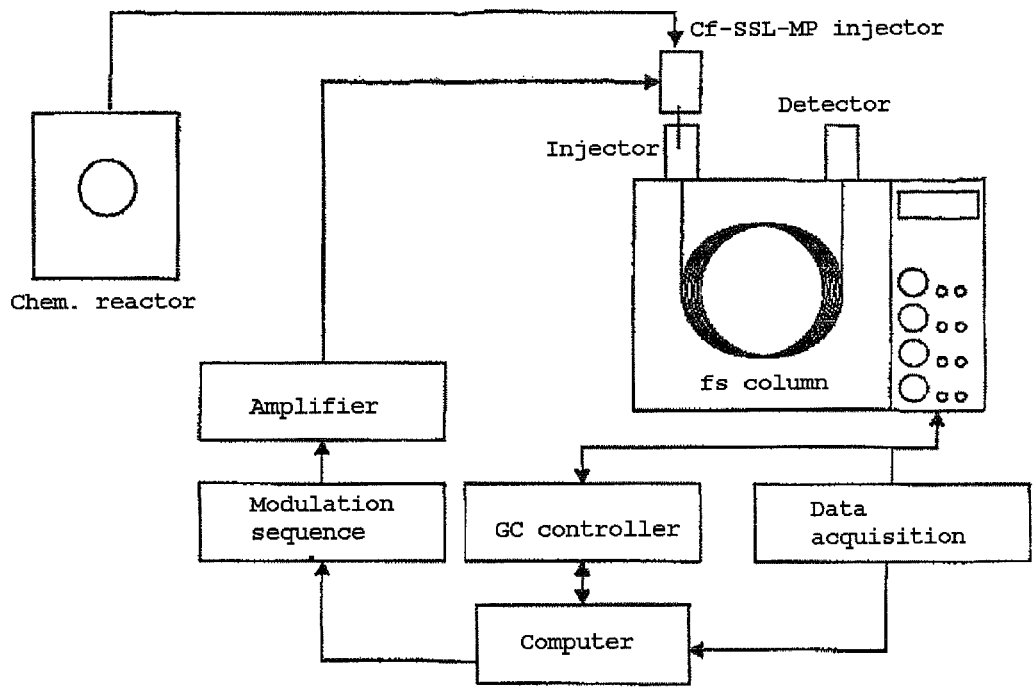
FIG. 1 shows a schematic of the principle of an exemplary embodiment of the fundamental design of an arrangement for carrying out an inventive analysis of substance mixtures.
Figure 2:
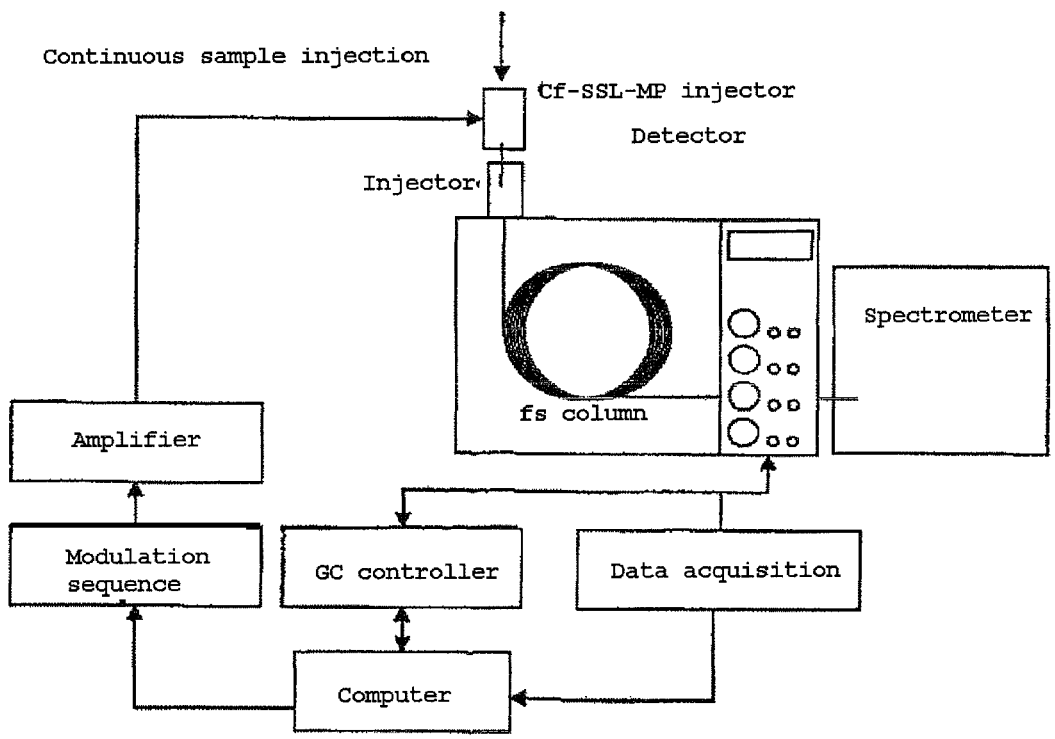
FIG. 2 shows a schematic of the principle of a further exemplary embodiment of the design in principle of an arrangement for carrying out an inventive analysis of substance mixtures.

The apparatus (injector cf-SSL-MP injector), used in FIG. 1 and FIG. 2, for generating pulsed substance mixtures can be connected, preferably for gas chromatography (GC) (compare FIG. 1 and FIG. 2) simply by being mounted on an existing split/splitless injector of the gas chromatograph. A corresponding application by means of Simple connection is also advantageously provided for supercritical fluid chromatography (SFC) not explicitly illustrated here.

FIG. 3 and FIGS. 4a to 4c as well as FIG. 5 and FIGS. 6a to 6c respectively show an exemplary embodiment of an inventive apparatus (injector, cf-SSL-MP injector) for generating pulsed substance mixtures. With the exemplary embodiment in FIG. 3 and FIGS. 4a to 4c, a substance mixture to be analyzed can be injected into a separating device. The exemplary embodiment in accordance with FIG. 5 and FIGS. 6a to 6c permits switched injection of up to seven substance mixtures.

The apparatuses (continuous split/splitless multiplexing injectors (cf-SSL-MP injector)) respectively consist of a heatable metal block (sample block) that is provided with bores for the respective injection channels—one injection channel in the exemplary embodiment in accordance with FIG. 3 and FIGS. 4a to 4c, and injection channels (sample channels) in the exemplary embodiment in accordance with FIG. 5 and FIGS. 6a to 6c. The injection channels accommodate capillary lines of the substance mixture respectively to be analyzed, that is to say of the respective sample source, preferably from a parallelized reactor, multititer plates or such a source. The substance mixtures (analytes) to be analyzed are fed continuously through the capillary lines consisting in the present case of metal, glass and/or fused silica glass, and vaporized in the sample block in a deactivated glass tube. To this end, the sample block has heating devices and thermocouples for exact temperature control. Superfluous vaporized substance mixtures (analytes) to be analyzed are discharged via flushing lines (backflushing). Each injection channel (sample channel) has a gas feed line that can be controlled by a high-speed pressure valve with switching times in the millisecond range. This gas feed line can also advantageously be used as a flushing line. The flushing can in this case also be controlled with the controllable or switchable pressure valve. Use may be made as gases of all inert gases and gas mixtures that lead to no variation in the analyte composition. The respective gas feed lines can be controlled individually and/or synchronously. A specific short pressure surge is used to inject the analyte mixture into a needle that is introduced into the existing split/splitless injector of the separating device, the gas chromatograph in the case of FIG. 1 and FIG. 2, and is heated there by the injector.

The respective configuration of the apparatuses for generating pulsed substance mixtures in accordance with FIG. 3 and FIGS. 4a to 4c, and FIG. 5 and FIGS. 6a to 6c, that is to say with an injection channel (sample channel) in the exemplary embodiment according to FIG. 3 and FIGS. 4a to 4c and with seven injection channels (sample channels) in the exemplary embodiment according to FIG. 5 and FIGS. 6a to 6c additionally permits over the possibility of flushing the injection needle by means of a carrier gas flow, in the region of ml/min in the present case, of the separating device (gas chromatograph). As a result, permanent flushing is achieved and contamination of the different substance mixtures (analyte mixtures) to be analyzed by means of multiplexing is avoided. Such an additional split flow can be set in the present case at the respective injection valves (backflushing) and/or at a split outlet integrated in the heating block. The entire split flow results from the sum of the respective flows at the valves. The volume between injection needle and vaporization space of the respective capillaries is advantageously minimized in such an arrangement, in particular in order to avoid dead volumes. Since, furthermore, this configuration of the apparatus means that the pressure surge takes place outside the injector of the separating device (gas chromatograph) and is absorbed by the pressure regulation of the separating device (gas chromatograph) or of the split system, there is advantageously no occurrence of pressure fluctuations in the separation by the apparatus (cf-SSL-MP injector).

Figure 7:
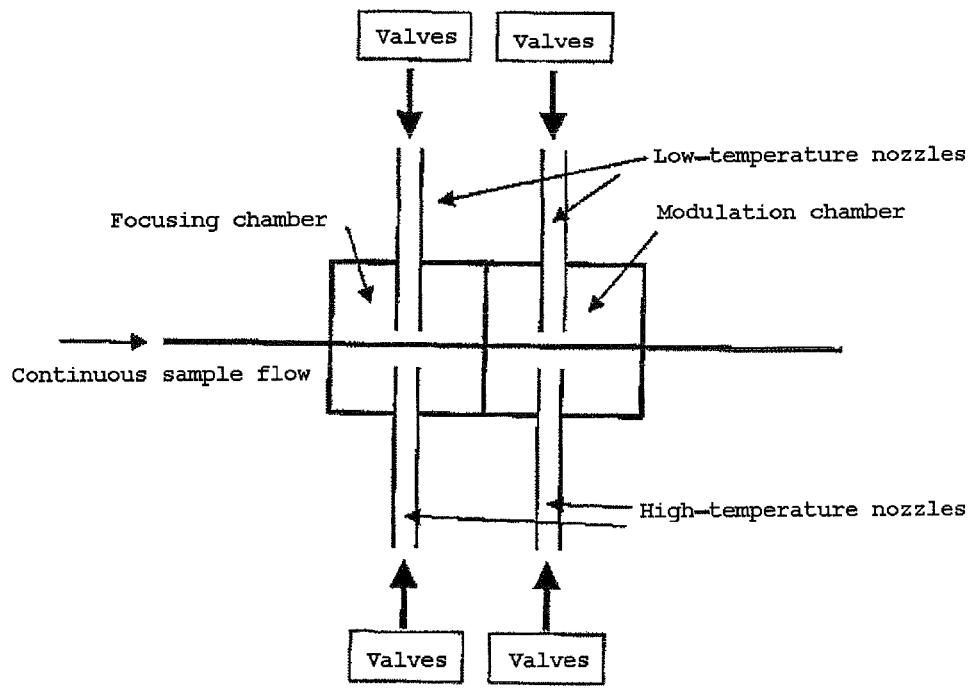
FIG. 7 shows a schematic of the design of a further exemplary embodiment of an inventive apparatus for generating pulsed substance mixtures.

FIG. 7 shows a further exemplary embodiment of an apparatus for generating pulsed substance mixtures. Here, the continuous flow of a substance mixture to be analyzed is modulated directly on the separating column of a separating device, in the present case of the gas chromatograph, as illustrated in FIG. 1 and FIG. 2, by a double focusing low-temperature modulator. The design principle illustrated in FIG. 7 permits here, in particular, an inventive coding of the substance mixture to be analyzed that can be used for two-dimensional separating techniques. As may be seen with the aid of FIG. 7, the column low-temperature modulator has two separate modulation chambers. The first chamber achieves the focusing of the substance mixture (analytes) to be analyzed, while in the second chamber the modulation of the substance mixture (analytes) to be analyzed is performed in accordance with a binary pseudorandom sequence that is generated by the computing device (computer) illustrated in FIG. 1 and FIG. 2, and/or by a separate device for generating an appropriate modulation sequence. By means of cold air and warm air jet nozzles with a volume flow of up to 40 l/min, the substance mixture (analytes) to be analyzed is firstly frozen out on the column by means of cold air and then released again by rapid heating by means of warm air. The jet nozzles of the apparatus (column low-temperature modulator) are driven in this case separately and independently of one another. It is true that the two chambers are synchronized in this case, but they are driven with different sequences. The control is advantageously performed such that no "dispersion" of the analytes on the column can occur.

Figure 8:
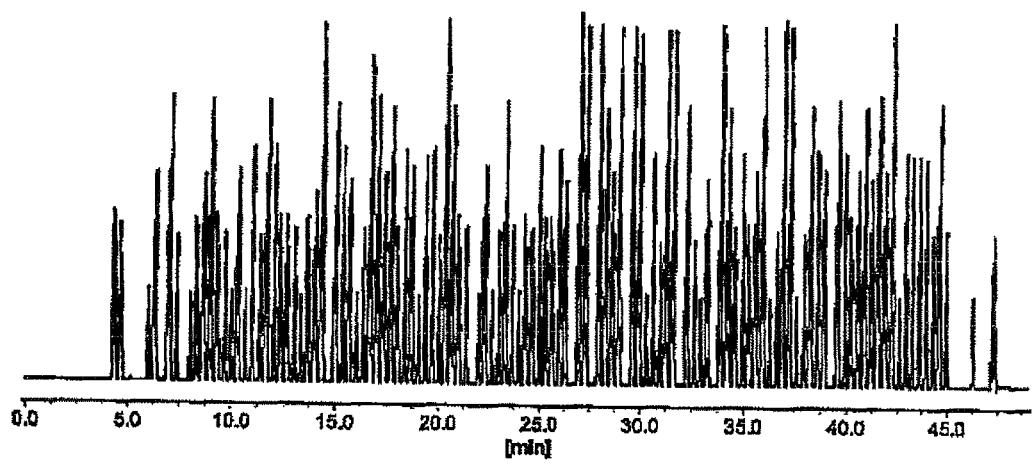
FIG. 8 shows a diagram of a measured injection stability of a unique binary sequence of a pulsed substance mixture with 127 pulses.
Figure 9:
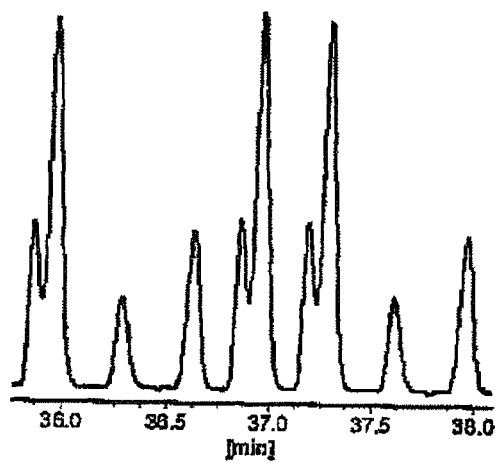
FIG. 9 shows an enlarged segment of the diagram according to FIG. 8.
Figure 10:
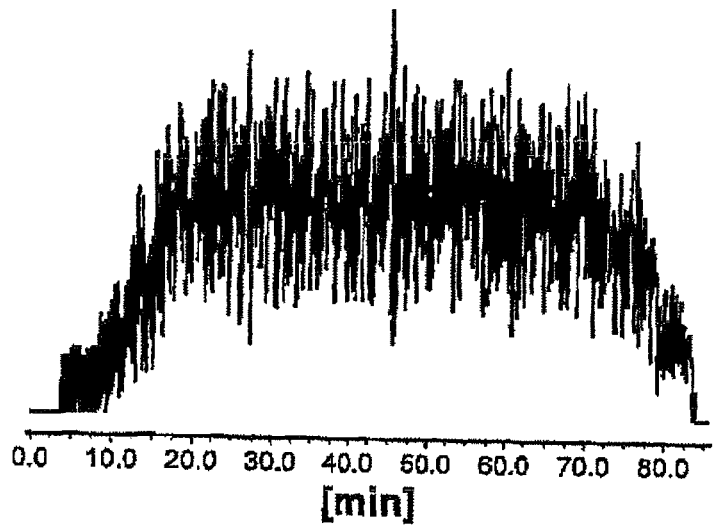
FIG. 10 shows a diagram of a measured injection stability of a unique binary sequence of a pulsed substance mixture with 2048 pulses.

FIG. 8 and FIG. 10 respectively show a diagram of a measured injection stability of a unique binary sequence of a pulsed substance mixture against time. Here, FIG. 8 shows the injection stability over a time period of 50 min of a 7-bit sequence (corresponding to $2^7=127$ elements) with an injection interval of $\Delta t=20$ s, a pulse duration of $\Delta t_{pulse}=10$ ms, given a 10 Hz data acquisition. FIG. 9 shows an enlarged segment of the diagram according to FIG. 8. The stability of the peak surfaces of three different substance mixtures (analytes) is clearly recognizable with the aid of FIG. 9. FIG. 10 shows the injection stability for short injection intervals with 1023 injections in 34 min of an 11-bit sequence (corresponding to $2^{11}=2048$ elements) with an injection interval of $\Delta t=1$ s, a pulse duration of $\Delta t_{pulse}=2$ ms, for a 10 Hz data acquisition.

As may be seen with the aid of FIGS. 8 to 10, it is possible to achieve exceptionally good injection stability even for short injection intervals, in particular injection intervals shorter than 400 ms, with the aid of the arrangements illustrated in FIGS. 1 to 7. Here, the pulse duration can even be maintained ($\Delta f = \Delta f_{pulse}$) with constant stability over the entire injection interval.

Since the pulse duration can be selected to be short as against the injection interval, multiple injection is advantageously possible within an injection interval (oversampling), as a result of which the throughput of substance mixtures to be analyzed (sample throughput) can be further raised.

Figure 11:
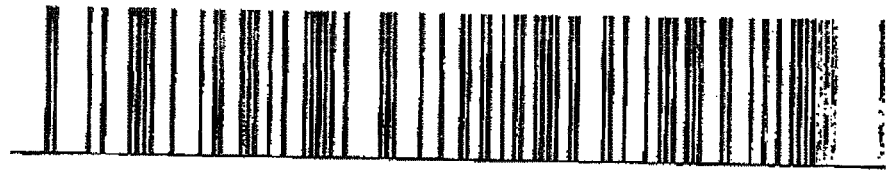
FIG. 11 shows a schematic of injection sections of substance mixtures to be analyzed within a unique binary sequence.

A high-throughput analysis can be implemented with the aid of the apparatus, illustrated in FIG. 5 and FIGS. 6a to 6c, for generating pulsed substance mixtures, particularly in conjunction with the arrangement, illustrated in FIG. 1, for analyzing substance mixtures. In this case, substance mixtures (analyte samples) to be analyzed are coded with a unique binary sequence. The coding of the analyte samples is performed by injecting the analytes in accordance with a binary pseudorandom sequence or a random sequence that consists of a pseudorandom sequence that is subdivided with a repeating sequence and has $2^n-x$ elements (x=1 in the case of Simplex and Hadamard matrices). The respective injection sections for the respective analyte samples can be of different length in this case in order to ensure an equivalent information content. FIG. 11 shows a schematic of corresponding injection sections for samples A1 to A13 within a binary pseudorandom sequence. The injection sequence consists of the same number of elements 0 and 1, or the number can differ by 1 ($2^n-1$).

The injection sections, illustrated by way of example in FIG. 11, of the samples A1 to A13 can additionally be split into calibration and measuring ranges in order to enable continuous quantification with internal standardization. An element 1 in the binary pseudorandom sequence in this case represents an injection in the form of an injection pulse. No injection takes place in the case of an element 0. The respective elements can, furthermore, be further split into submodulation sequences that are of similar structure for all the elements, advantageously in order to ensure multiple injections (oversampling).

Each substance mixture (sample) to be analyzed is advantageously injected multiply in sequence during analysis in order to enable a quantification of the respective component. The minimum number of required injections for uniquely identifying and quantifying the individual analytes in a mixture can be determined in this case with the aid of the following characteristic variables:

Number of samples: $I_{max}$
Number of analytes in a sample: $k_{max}$
Number of time intervals $\Delta t[s]$ from the modulation sequence of length n: $N=2^n-1$
Data acquisition frequency and/or injection frequency (oversampling) per time interval: $f_{OVR}$
Maximum retention time: $r_R^{max}$ [min]
Maximum number of analyzable samples:

$$i_{max} = \frac{\left(N + \frac{t_R^{max}}{60\Delta t}\right)}{k_{max}} f_{OVR}$$

Number of required repetition injections per sample:

$$n_{injections} = \frac{N}{2 \cdot i_{max}} = \frac{N \cdot k_{max}}{2\left(N + \frac{t_R^{max}}{60\Delta t}\right) f_{OVR}}$$

Total analysis period:

$$t_{analysis\ period} = \frac{\frac{N \cdot \Delta t}{60} + t_R^{max}}{i_{max}}$$

Sample throughput:

$$P = \frac{i_{max}}{t_{analysis\ period}} = \frac{i_{max}^2}{\left(\frac{N \cdot \Delta t}{60} + t_R^{max}\right)} = \frac{\left(N + \frac{t_R^{max}}{60\Delta t}\right) \cdot i_{max}}{k_{max}\left(\frac{N \cdot \Delta t}{60} + t_R^{max}\right)}$$

Particularly in conjunction with the arrangement, illustrated in FIG. 2, for analyzing substance mixtures, it is possible to implement a high-resolution analysis with the aid of the apparatuses, illustrated in FIGS. 3 and 4a to 4c and in FIG. 7, for generating pulsed substance mixtures (low-temperature modulation). In this case, a substance mixture (analyte sample) to be analyzed is coded with a unique binary sequence. The coding of the analyte sample is performed by injection apparatus in accordance with FIG. 3 and FIGS. 4a to 4c or low-temperature modulation (apparatus in accordance with FIG. 7) of the analyte sample in accordance with a binary pseudorandom sequence or a random sequence that consists of a pseudorandom sequence subdivided with a repeating sequence, which has $2^n-x$ elements (x=1 in the case of Simplex and Hadamard matrices). The injection sequence consists of the same number of the elements 0 and 1, or the number can differ by 1 ($2^n-1$). In the case of an element 1, a sample is injected or released by the hot air jet. In the case of an element 0, no injection is performed or there is freezing in by the cold air jet. The injection intervals are selected in accordance with the time required for a so-called full scan or a multiple of the duration of a so-called full scan of the spectrometer. The scanning (detection) of the spectrometer and the injection interval are synchronized with one another in this case. The injection pulse duration or modulation period in the case of the low-temperature modulator can be selected to be equal to or shorter than the injection interval or the modulation interval. It is also advantageously possible to carry out different spectroscopic or spectrometric experiments in each injection interval or modulation interval. A mass full scan and MS/MS or MS$^n$ experiments for unique identification and quantification are preferably performed.

Figure 12:
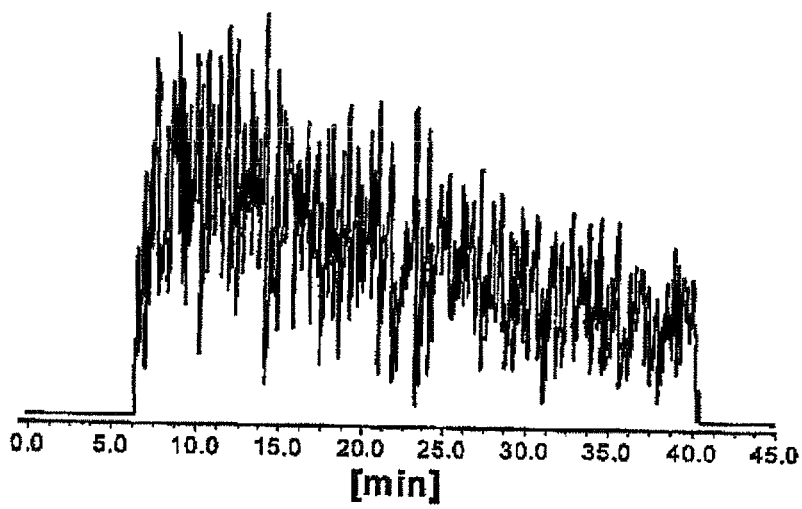
FIG. 12 shows a diagram of the detected concentration change in a substance mixture to be analyzed.

FIG. 12 shows a diagram of the gradual time change in concentration of a substance mixture (analytes) to be analyzed, in the form of an entire chromatogram acquired by the evaluation device. The appropriate data of the entire chromatogram are provided by the evaluation device and/or by a data acquisition device connected thereto (compare FIG. 1 and FIG. 2). The raw data are used for the further evaluation by means of a computing device (computer) of the evaluation device, particularly in the course of a deconvolution for further evaluation.

Figure 13:
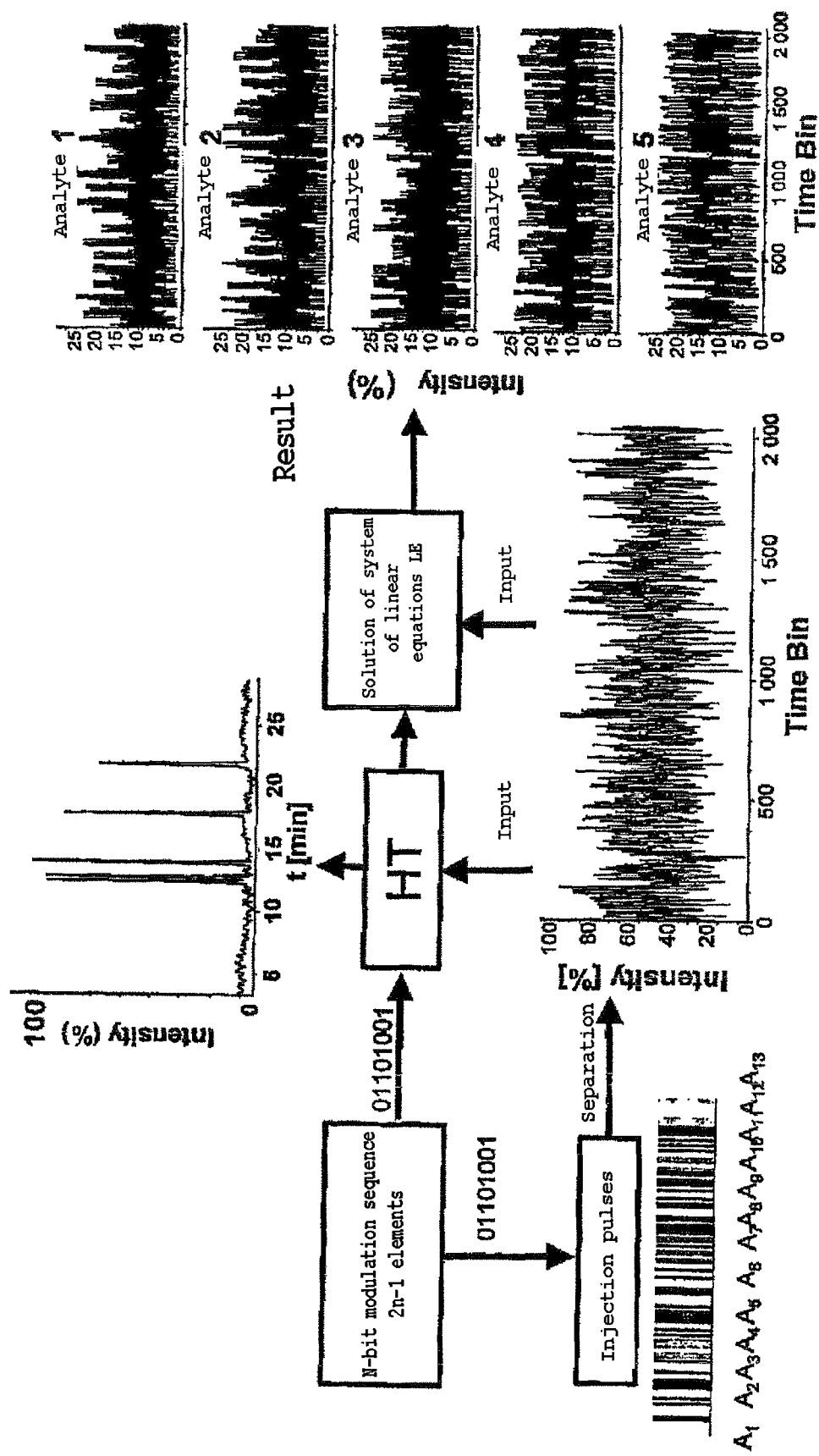
FIG. 13 shows a schematic of the sequence of an inventive analysis.

The sequence of an inventive analysis of a substance mixture is illustrated symbolically in FIG. 13. The evaluation of the analysis is performed by using a deconvolution method. The deconvolution method has the following three steps:
1. deconvolution of the raw data with the inverse coding matrix, in order to obtain the entire chromatogram;
2. calculation of the relative concentration distribution of the individual analytes from step 1, and filling the concentration distribution matrix and the concentration vector of the individual analytes; and
3. solving the system of linear equations in order to determine the concentrations of the individual analytes.

The modulation of n analyte injections uses an entire chromatogram (compare FIG. 12 and FIG. 13) that represents a superposition of n individual chromatograms. The direct multiplication of the raw data in the circular representation (after $2^n-1$ time intervals, the signal intensity is added again to the vector elements at the beginning) by the inverse Hadamard, Simplex or inverse matrix of the known binary pseudorandom sequence uses the entire chromatogram (compare FIG. 13) of the respective analytes.

The entire chromatogram yields, on the one hand, the number $k_{max}$ of the different analytes in the respective samples i, and the respective peak forms. In this case, a very good resolution of the peaks is attained with the inventive refinements of the analysis method, and so it is also possible to apply the method to problems with small separation factors such as occur, for example, in the case of enantiomeric separations for determining the enantiomeric excess ee.

Since the Hadamard transformation cannot take account of any analyte fluctuations, this entire chromatogram (compare FIG. 12) is characterized by deviations in the base line which, however, in turn represents a convolution of the respective analyte concentrations. Consequently, the first step is to carry out a peak form analysis in order to obtain the distribution function $\Psi(A_k)$ of the respective analytes as a function of time. Here, the maximum of each individual analyte peak is normalized to 1. The concentration distribution matrix is therefore subsequently filled, specifically in such a way that each column has the relative concentration $\Psi(A_{i,j,k})$ of the analyte $A_k$ of the ith sample and jth repeat injection as a function of the injection sequence and the time interval $\Delta t$, as follows:

$$\text{Chromatogramm} = ij \sum_{k=1}^{k_{max}} \Psi(A_k)$$

$$= \begin{bmatrix} \Psi(A_1(1)) & \Psi(A_2(1)) & \Psi(A_3(1)) & \cdots & \cdots & \cdots & \cdots & \Psi(A_k(1)) \\ \Psi(A_1(2)) & \Psi(A_2(2)) & \Psi(A_3(2)) & & & & & \vdots \\ \Psi(A_1(3)) & \Psi(A_2(3)) & \Psi(A_3(3)) & & & & & \vdots \\ \vdots & & & \ddots & & & & \vdots \\ \vdots & & & & \ddots & & & \vdots \\ \vdots & & & & & \Psi(A_{k-2}(t-2)) & \Psi(A_{k-1}(t-2)) & \Psi(A_k(t-2)) \\ \vdots & & & & & \Psi(A_{k-2}(t-1)) & \Psi(A_{k-1}(t-1)) & \Psi(A_k(t-1)) \\ \Psi(A_1(t)) & \cdots & \cdots & \cdots & \cdots & \Psi(A_{k-2}(t)) & \Psi(A_{k-1}(t)) & \Psi(A_k(t)) \end{bmatrix}$$

$$\begin{bmatrix} A_{1,1,1} \\ A_{i,1,1} \\ A_{1,2,1} \\ A_{i,j,1} \\ A_{1,1,2} \\ A_{i,1,2} \\ A_{i,j,2} \\ A_{i,j,k} \end{bmatrix}$$

$$= \begin{bmatrix} I_1 \\ \vdots \\ \vdots \\ \vdots \\ \vdots \\ \vdots \\ \vdots \\ I_t \end{bmatrix}$$

Each row constitutes in this case the sum of the relative concentrations of the respective analytes in the samples. This mode of procedure can be applied to the raw chromatogram in the circular and noncircular representation. The respective concentration of the analytes is yielded as a concentration vector that, when multiplied by the concentration distribution matrix, yields the signal intensities in each time interval of the raw chromatogram. The result is thus a system of linear equations in a matrix representation that can be solved by iteratively eliminating variables or by applying the Gauβ-Jordan method.

The solution is the concentration of the respective analytes in the samples i. In order to optimize, check and assess the quality of the solution thus obtained for the system of equations, the raw chromatogram is transformed into an entire chromatogram by means of iterative adaptation using the concentration vector (by forming the difference or by dividing) and subsequent Hadamard transformation, the deviations thereof in the base line being minimized by further fine tuning steps in the solution of the system of linear equations.

On the right-hand side, FIG. 13 shows the concentration of the analytes of the respective samples in a circular representation. The concentrations of the analytes in the individual samples are obtained by circular displacement in accordance with the binary pseudorandom sequence and the respective time interval. These concentration data can be further processed with further absolute concentrations or relative concentrations, preferably by using an internal standardization.

Figure 14:
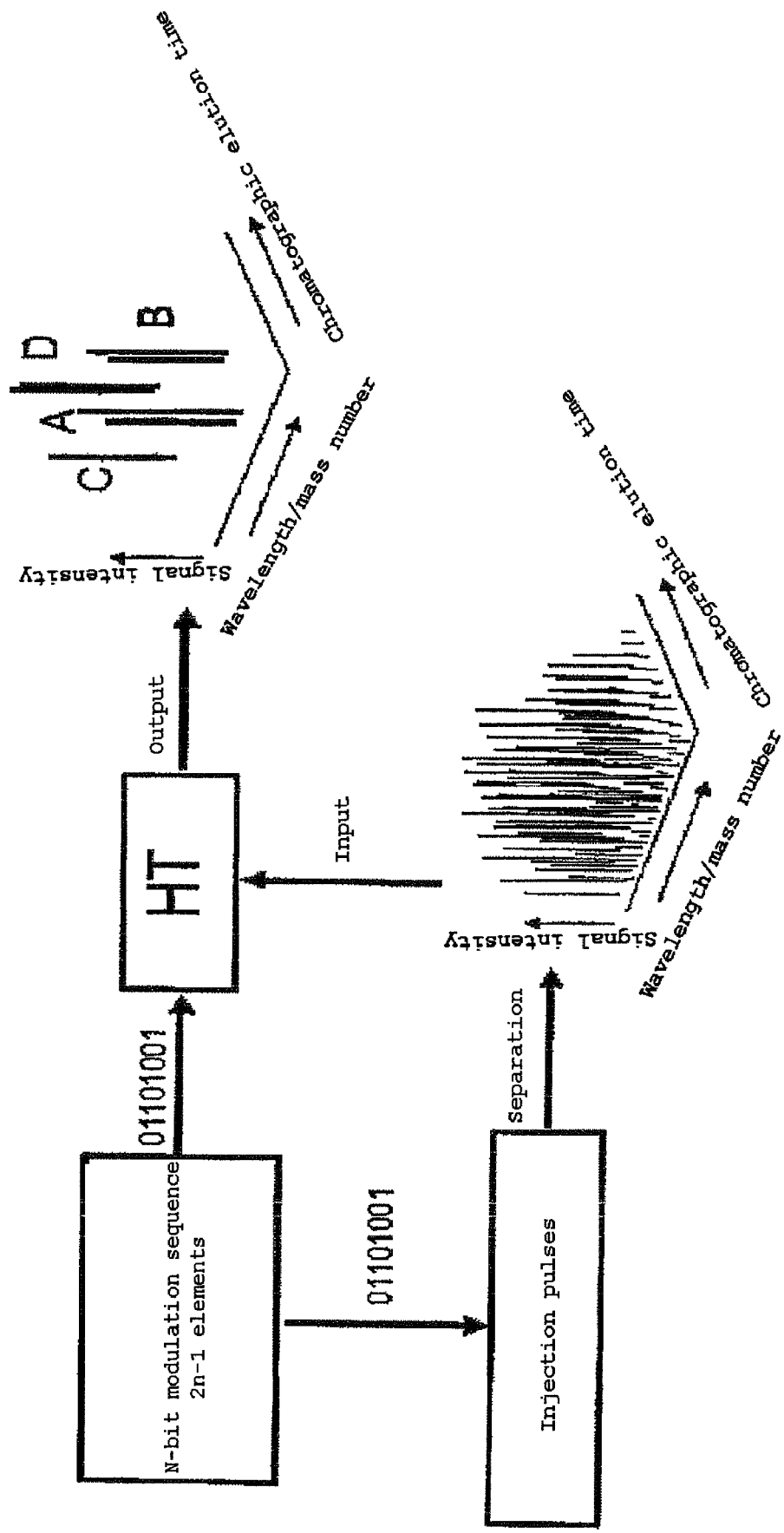
FIG. 14 shows a further schematic of the sequence of an inventive analysis.

On the basis of the example, illustrated by way of example in the diagram shown in FIG. 14, of an inventive analysis of a substance mixture, the use of two-dimensional detection and evaluation can be identified. The spectra of the substance mixture are identified in the deconvolution method put to use in this case. The deconvolution method has the following steps:

1. Extraction of the respective wave number or mass/charge ratio from all the spectra detected by the evaluation device, and
2. Hadamard transformation with the known pseudorandom sequence.

The spectra relating to the respective peaks in the conventional chromatogram are yielded therefrom with an improved signal-to-noise ratio (SNR) and shortened analysis periods.

The exemplary embodiments, illustrated in the figures of the drawing, of the invention serve merely to explain the invention and do not limit the latter.

The invention claimed is:

1. A method for analyzing a plurality of substance mixtures, comprising feeding said plurality of substance mixtures to be analyzed to a separating device, separating the substances of the substance mixture to be analyzed from one another by the separating device by chemically and/or physically effected transport, and detecting the separated substances by an evaluation device, wherein said feeding comprises feeding each substance mixture to be analyzed to the separating device in pulses of a unique binary sequence; and wherein each substance mixture to be analyzed is injected multiple times in sequence during analysis in order to identify and quantify individual analytes in each substance mixture.

2. The method as claimed in claim 1, which further comprises feeding the pulses of the substance mixtures to be analyzed to the separating device in a fashion temporally and spatially separated from one another.

3. The method as claimed in claim 1, wherein the unique binary sequence is produced by a binary random number generator.

4. The method as claimed in claim 1, wherein the unique binary sequence is formed from a sequence that is subdivided by a repeating sequence and generated with a binary random number generator.

5. The method as claimed in claim 1, wherein the unique binary sequence consists of $2^n$ elements, with $0 \leq n \leq \infty$.

6. The method as claimed in claim 1, wherein the pulses are at a modulation interval ($\Delta t$) in a range from approximately 0.25 s to approximately 120 ss.

7. The method as claimed claim 1, wherein the pulses are at a pulse duration ($\Delta t_{pulse}$) in a range from approximately 1 ms to approximately 1 s.

8. The method as claimed in claim 1, wherein said detecting is performed by the evaluation device in a fashion synchronized with a substance mixture feed.

9. The method as claimed in claim 8, wherein the substances detected by the evaluation device are deconvoluted mathematically with the unique binary sequence of the pulses of the substance mixture to be analyzed.

10. The method as claimed in claim 9, wherein, in the course of the deconvolution, the substances detected by the evaluation device are subjected to a Hadamard transformation with the unique binary sequence, concentration distributions of the substances detected by the evaluation device are determined from the result of the Hadamard transformation, and concentrations of the individual substances detected by the evaluation device are determined.

11. The method as claimed in claim 1, wherein the evaluation device is operated with a detection period that corresponds to a modulation interval (pulse interval duration $\Delta t$) or to an integral fraction of the modulation interval (pulse interval duration $\Delta t$).

12. The method as claimed in claim 1, wherein the separating device uses chromatographic and/or electrophoretic separating methods.

13. The method as claimed in claim 1, wherein the evaluation device comprises at least one detector.

* * * * *